(12) United States Patent
Bhattacharjee et al.

(10) Patent No.: US 10,445,713 B2
(45) Date of Patent: Oct. 15, 2019

(54) MOBILE-COMPATIBLE OFFERING OF COMMERCIALLY IDENTICAL ITEMS FOR POST-RETAIL SALE

(71) Applicant: MasterCard International Incorporated, Purchase, NY (US)

(72) Inventors: Manash Bhattacharjee, Jersey City, NJ (US); Debashis Ghosh, Charlotte, NC (US)

(73) Assignee: MASTERCARD INTERNATIONAL INCORPORATED, Purchase, NY (US)

( * ) Notice: Subject to any disclaimer, the term of this patent is extended or adjusted under 35 U.S.C. 154(b) by 847 days.

(21) Appl. No.: 14/845,160

(22) Filed: Sep. 3, 2015

(65) Prior Publication Data
US 2017/0068944 A1 Mar. 9, 2017

(51) Int. Cl.
| | |
|---|---|
| G06Q 20/20 | (2012.01) |
| G06F 19/00 | (2018.01) |
| G06Q 20/32 | (2012.01) |
| G06Q 50/22 | (2018.01) |
| H04W 4/02 | (2018.01) |

(52) U.S. Cl.
CPC ....... *G06Q 20/204* (2013.01); *G06F 19/3456* (2013.01); *G06Q 20/3224* (2013.01); *G06Q 20/3278* (2013.01); *G06Q 50/22* (2013.01); *H04W 4/02* (2013.01)

(58) Field of Classification Search
USPC ......................................................... 705/28
See application file for complete search history.

(56) References Cited

U.S. PATENT DOCUMENTS

| | | | |
|---|---|---|---|
| 8,108,318 | B2 | 1/2012 | Mardikar |
| 8,738,454 | B2 | 5/2014 | Argue et al. |
| 8,831,981 | B2 | 9/2014 | Cheng |
| 8,942,992 | B1 | 1/2015 | Zhu |
| 9,064,247 | B2 | 6/2015 | Baer et al. |
| 2003/0101071 | A1 | 5/2003 | Salonen |
| 2004/0215485 | A1 | 10/2004 | Lasorsa |
| 2007/0022019 | A1 | 1/2007 | Sherwin et al. |
| 2010/0153204 | A1 | 6/2010 | Shaw et al. |
| 2011/0035321 | A1* | 2/2011 | Ching ............... G06Q 20/20 705/75 |
| 2011/0307342 | A1 | 12/2011 | Haji |
| 2012/0054050 | A1 | 3/2012 | Ziegler et al. |
| 2012/0185306 | A1 | 7/2012 | Cheng |
| 2012/0203656 | A1 | 8/2012 | Schuh et al. |
| 2014/0143137 | A1 | 5/2014 | Carlson |
| 2014/0166523 | A1 | 6/2014 | Williams-Hartman |

(Continued)

FOREIGN PATENT DOCUMENTS

JP       2003-208474 A       7/2003

OTHER PUBLICATIONS

Apple Pay Makes NFC Relevant, Flomio, (2014) accessed on Jun. 30, 2015, available at: flomio.com/2014/10/apple-pay-makes-nfc-relevant/. (4 pages).

(Continued)

*Primary Examiner* — Garcia Ade
(74) *Attorney, Agent, or Firm* — Ballard Spahr LLP (57) ABSTRACT

Systems and methods for pairing a mobile app with a point-of-sale system and recording an availability of units from a retail package are described.

10 Claims, 7 Drawing Sheets

(56) References Cited

U.S. PATENT DOCUMENTS

| | | | | |
|---|---|---|---|---|
| 2014/0249916 | A1 | 9/2014 | Verhaeghe | |
| 2014/0258051 | A1* | 9/2014 | Bostwick | G06Q 20/203 705/28 |
| 2015/0088643 | A1 | 3/2015 | Shuken et al. | |
| 2015/0154590 | A1 | 6/2015 | Ghosh et al. | |
| 2015/0172473 | A1 | 6/2015 | Estrada et al. | |

OTHER PUBLICATIONS

Bluetooth Pairing Service Overview, Microsoft (2008) accessed on Jun. 10, 2015, available at: https://msdn.microsoft.com/en-us/library/cc51. (2 pages).

Contactless Toolkit for Merchants, MasterCard, Inc., (2015) available at: www.mastercard.com/contactless/doc/MC%20Contactless_Toolkit_Merchants_Global 2015(final).pdf. (16 pages).

eThor API Interactive Documentation, eThor.com, accessed on Jun. 10, 2015, available at: http://ethor.com/api-docs/overview.html. (5 pages).

Freed-Finnegan, et al., "Apple Pay 'no-data-collection' isn't a feature. Its a problem," Venture Beat, (2014) accessed on Jun. 29, 2015, available at venturebeat.com/2014/10/27/apple-pay-no-data-collection-isnt-a-feature-its-a-problem/. (5 pages).

Green Receipt Dispenser: NFC User Guide Version 0.1, Mirano, available at: www.mirano.ca/pdfs/GPD-SM-PRD-UG-004.pdf. (17 pages).

Green Receipt Dispenser: Quick Install Guide (Plug N Play) Version 0.2, Mirano, available at: www.mirano.ca/pdfs/GPD-SM-PRD-UG-003.pdf. (18 pages).

Ho, et al., Digital Receipts: Fostering Mobile Payment Adoption, Lecture Notes in Computer Science, vol. 8309, 2013, pp. 140-149.

Host Card Emulation (HCE) 101, A Smart Card Alliance Mobile & NFC Council White Paper, (2014) Publication No. MNFCC-14002, available at: www.smartcardalliance.org/wp-content/uploads/HCE-101-WP-FINAL-081114-clean.pdf. (32 pages).

MasterCard Best Practices for Mobile Point of Sale Acceptance: A guide to enabling acceptance on mobile devices, MasterCard, Inc., (2013) available at: www.mastercard.com/us/company/en/docs/MasterCard_Mobile_Point_Of_Sale_Best_Practices.pdf. (15 pages).

NFC Payments and the Point of Sale: White Paper, VeriFone, (2011) available at: verifonezone.com/fstore/0a463145bbfccb42_-6b6a8b6a_131622799b3_-6202/Nfc%20Primer%20White%20Paper.pdf. (12 pages).

NFC: Facts at a Glance, Smart Card Alliance, (2011) available at: www.smartcardalliance.org/resources/pdf/NFC_Facts_at_a_Glance_060711.pdf. (3 pages).

POS Integration Becoming a "Must-Have", Hospitality Technology, (2014) available at: hospitalitytechnology.edgl.com/print?printpath=/HT/News/Industry-News/Industry-News/POS-Integration-Becoming-a-Must-Have&classname=CMS.Article. (3 pages).

Rodgers, Dirk, A Closer Look at Web Portals for DSCSA Transaction Data Exchange, RXtrace.com, (2014) available at: http://www.rxtrace.com/2014/12/a-closer-look-at-web-portals-for-dscsa-transaction-data-exchange.html/. (3 pages).

Rosenberg, Einar, 10 Things you (and maybe Google!) didn't know Google Wallet can do, Mobile Payments Today: Technology, Trends, and Insights, accessed on Jun. 29, 2015, available at: www.mobilepaymentstoday.com/blogs/10-things-you-and-maybe-google-didnt-know-google-wallet-can-do/. (4 pages).

Sharing Insights into the world of Restaurant POS, lonetreerob, accessed on Jun. 25, 2015, available at: lonetreerob.wordpress.com. (13 pages).

International Search Report and Written Opinion dated Aug. 30, 2016 for application PCT/US2016/036389, filed on Jun. 8, 2016 (Applicant—MasterCard Int'l, Inc. // Inventor—Bhattacharjee, et al.) (9 pages).

* cited by examiner

MOBILE-COMPATIBLE OFFERING OF COMMERCIALLY IDENTICAL ITEMS FOR POST-RETAIL SALE

BACKGROUND

Field of the Disclosure

Aspects of the disclosure relate in general to mobile data communications and support for post-retail sales.

Description of the Related Art

The recent and widespread availability of mobile interconnectivity has supported the rise of a sharing economy. One example of this trend is the Uber mobile app, which allows vehicle owners to capitalize on unused capacity of their vehicles. Another example is the Airbnb mobile app, which allows homeowners and apartment renters to capitalize on unused capacity of their residences. Thus far, however, such mobile-ready capitalization has been limited to shared use of large investments.

SUMMARY

A method, according to a general configuration, of pairing a mobile app with a point-of-sale system and recording an availability of units from a retail package is described. This method includes receiving information indicating a current location of a mobile device; based on the indicated location, selecting a point-of-sale (POS) system; transmitting, to the selected POS system, information that identifies a mobile app resident on the mobile device; receiving, from at least one among the POS system and the mobile device, an indication of a retail package that includes a plurality of commercially identical items; and receiving, from the mobile app resident on the mobile device, an indication of a quantity of the commercially identical items. A middle layer configured to perform such a method is also disclosed. Computer-readable storage media (e.g., non-transitory media) having instructions that cause one or more processors executing the instructions to perform such a method are also disclosed.

An apparatus, according to a general configuration, for pairing a mobile app with a point-of-sale system and recording an availability of units from a retail package is described. The apparatus includes a pairing service configured to receive information indicating a current location of a mobile device; to select, based on the indicated location, a point-of-sale (POS) system; and to transmit, to the selected POS system, information that identifies a mobile app resident on the mobile device. The apparatus also includes a transaction data exchange service configured to receive, from at least one among the POS system and the mobile device, an indication of a retail package that includes a plurality of commercially identical items; and to receive, from the mobile app resident on the mobile device, an indication of a quantity of the commercially identical items.

A method, according to another general configuration, of using a mobile device to purchase a retail package and to update an inventory that indicates subunits of the retail package is described. This method includes using a mobile device to transmit payment information for a transaction to a point-of-sale system; using the mobile device to receive purchase information for the transaction from the point-of-sale system that identifies a retail package purchased in the transaction, the retail package including a plurality of commercially identical items; using the mobile device to select a quantity of the commercially identical items of the retail package; and using the mobile device to transmit a command to update an inventory associated with the mobile device to include the selected quantity of the commercially identical items. A mobile device configured to perform such a method is also disclosed. Computer-readable storage media (e.g., non-transitory media) having instructions that cause one or more processors executing the instructions to perform such a method are also disclosed.

An apparatus, according to another general configuration, for purchasing a retail package and updating an inventory that indicates subunits of the retail package is described. The apparatus includes a digital wallet configured to transmit payment information for a transaction to a point-of-sale system. The apparatus also includes a mobile app configured to receive purchase information for the transaction from the point-of-sale system that identifies a retail package purchased in the transaction, the retail package including a plurality of commercially identical items; to select a quantity of the commercially identical items of the retail package; and to transmit a command to update an inventory associated with the mobile device to include the selected quantity of the commercially identical items.

A method, according to another general configuration, of maintaining an inventory of items and corresponding providers and of responding to customer requests relating to the items is described. This method includes receiving a first text message, from a first subscriber number, that identifies a provider, an item, and a quantity of commercially identical units within the item; receiving a second text message, from a second subscriber number, that indicates a request relating to the item; and transmitting, to the second subscriber number, a response to the request. A system configured to perform such a method is also disclosed. Computer-readable storage media (e.g., non-transitory media) having instructions that cause one or more processors executing the instructions to perform such a method are also disclosed.

An apparatus, according to another general configuration, for maintaining an inventory of items and corresponding providers and of responding to customer requests relating to the items is described. The apparatus includes a database management service configured to update an inventory in response to receiving a first text message, from a first subscriber number, that identifies a provider, an item, and a quantity of commercially identical units within the item. The apparatus also includes an interface configured to transmit to a second subscriber number, in response to receiving a second text message, from the second subscriber number, that indicates a request relating to the item, a response to the request.

DETAILED DESCRIPTION

Many products are packaged for retail purchase (e.g., by an end-user consumer) as a bulk package that includes a number of commercially identical units but is identified as a single item for retail purchase. One example of such a bulk package is a bottle or other container of pills. In other cases, a retail package may contain a number of commercially identical items that are packed individually in bags or other wrappers. Examples of such packages include a package of six, twelve, or twenty-four cans of soda; a box of ten bags of microwave popcorn; and a box of twelve packages of instant ramen noodles.

Such a bulk package is typically tagged with a single instance of a corresponding retail tracking identifier (e.g., a Universal Product Code (UPC) barcode or radio-frequency identification (RFID) item-level tag) for the package. The individual component units may bear identifying information (e.g., name) and/or other information such as expiration date (e.g., on a contraceptive wrapper), but typically lack any such retail tracking identifier.

Such bulk packaging may be found among personal care products, including over-the-counter medications, feminine hygiene products, and non-prescription contraceptives. Examples of over-the-counter medications may include pain relievers (e.g., aspirin, ibuprofen, acetaminophen (also called paracetamol)), laxatives, antidiarrheals, decongestants, antihistamines, and cough suppressors (e.g., cough drops). Such medications may be retail packaged, for example, as a bottle or other container of pills or as a blister pack having one or more pills in each compartment. Examples of feminine hygiene products may include tampons and sanitary napkins (also called sanitary pads or menstrual pads). Examples of non-prescription contraceptives may include condoms and contraceptive sponges. Other examples of bulk packaged personal care products include absorbent products (such as diapers and incontinence products), adhesive bandages, and oral hygiene products (e.g., dental flossers).

The marginal cost of each component unit within such a bulk package will typically decrease as the number of units in the package increases. For example, the cost per pill (e.g., tablet or capsule) in a bottle of an over-the-counter medication (e.g., a pain reliever) will typically be much less for a bottle of one hundred pills than for a bottle of twenty-four pills. Nevertheless, purchase of the larger package may represent a significant one-time expense for the consumer. Moreover, the product will commonly have an expiration date (especially for foodstuffs and medications). For a retail purchaser who uses the product only occasionally, the initial potential savings may evaporate or even be reversed if the product expires before all of its units are consumed.

Systems and methods as described herein may be used to support resale of such unused capacity to other consumers. Such resale may reduce risk associated with the initial capital outlay and/or increase availability of the product within a corresponding population. Particular contemplated applications include dense populations of people having a similar demand for the product (e.g., a college dormitory or similar residential compound) and clustered populations that may be too small to support a traditional retail presence (e.g., a village in a developing economy).

Leveraging the availability of smartphones and/or feature phones, an ecosystem may be created for people to buy over-the-counter medications, oral hygiene, feminine hygiene, contraceptive, and/or other personal care products from other individuals on-demand and/or in an emergency situation. Such practice may help to reduce wastage of products that are predominantly sold in bulk and might not be consumed by the customer entirely before expiring.

It may be desired to provide a system to enable anyone with a smartphone to manually scan and upload a stock of over-the-counter medications and quantities, using a mobile app and/or a web portal. Additionally or in the alternative to such manual loading of products by a user provider to the online inventory, an automated process may be created to add products to the user's online inventory at the time of checkout when the user purchases items at the store. This scenario may be enabled, for example, by using a middle layer that can integrate with different POS systems present at both large medical stores as well as general retail stores, for over-the-counter medications and/or other personal care products.

Figure 1A:
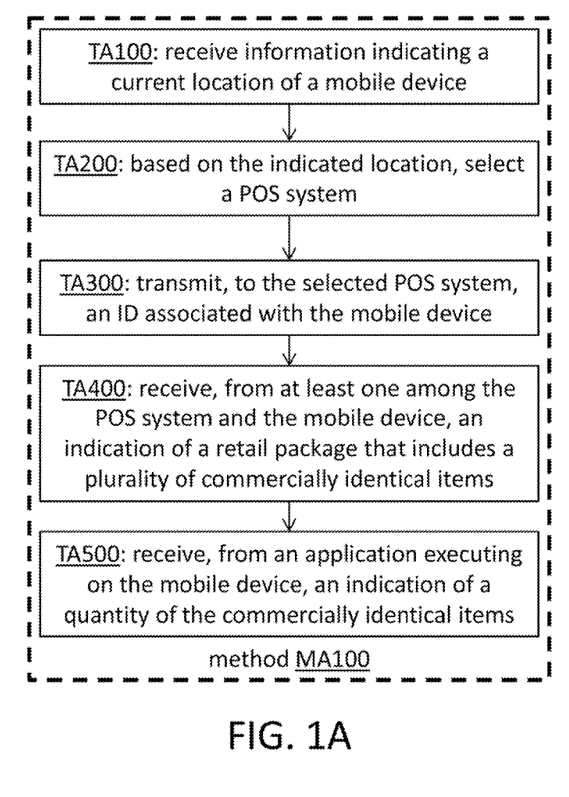
FIG. 1A shows a flowchart of a method MA100 of pairing a mobile app with a point-of-sale system and recording an availability of sub-units of a purchased retail package.

FIG. 1A shows a flowchart of a method MA100 of pairing a mobile app with a point-of-sale system and recording an availability of units from a retail package. Such a method may be performed, for example, by a middle layer as described below.

Method MA100 includes tasks TA100, TA200, TA300, and TA400. Task TA100 receives information indicating a current location of a mobile device. In one example, the location is in the form of GPS coordinates. In a typical implementation, task TA100 receives the location information via one or more data networks, such as one or more cellular data networks (e.g., 2G, 3G, 4G, LTE, etc.) and/or one or more local- and/or wide-area wireless data networks (e.g., IEEE 802.11 or WiFi).

Based on the indicated location, task TA200 selects a point-of-sale (POS) system. For example, task TA200 may be implemented to select, from among a plurality of POS systems whose locations are known, the POS system closest to the indicated location. The known location of a POS system may be recorded as a location (e.g., in GPS coordinates) of a retail establishment at which the POS system is found. The plurality of POS systems may be limited to POS systems of a particular retailer or may include POS systems of a plurality of retailers. For example, task TA200 may be implemented to select a POS system of a retailer only if the mobile device is currently associated with an account of a loyalty program of the retailer. Such an association may be recorded, for example, in a database entry that corresponds to the mobile device (e.g., a corresponding entry of an implementation of provider database VDB100 as described below).

Task TA300 transmits, to the selected point-of-sale system, information that identifies a mobile app which is resident on the mobile device. Such information distinguishes the mobile app from other instances of the same software that may be resident on other mobile devices. The information may be a label that identifies, for example, a particular payment account (e.g., a credit card account number), or a particular account of a loyalty program of a retailer (e.g., the retailer associated with the selected POS system), where the particular account has already been associated with the mobile app. The POS system may be configured to use such information to associate a particular transaction with the mobile application so that information relating to the transaction (e.g., a receipt) may be directed to the mobile application. Task TA300 may be included within an activity of pairing the mobile app and the POS system (e.g., as described herein with reference to pairing service PSV100).

Task TA400 receives, from at least one among the POS system and the mobile device, an indicator of a retail package that includes a plurality of commercially identical items. The receipt of this indicator (e.g., the name and/or product code of the retail package) typically indicates that the mobile app has been used to purchase the retail package via the POS system. If the package indicator is received from the POS system, task TA400 may include forwarding the package indicator to the mobile app. Alternatively, the POS system may be configured to send the package indicator directly to the mobile app (e.g., via SMS, or to an e-mail address or URL associated with the mobile app), such as included in a receipt for the transaction, in which case task TA400 may then receive the package indicator from the mobile app.

Task TA500 receives, from the mobile app resident on the mobile device, an indication of a quantity of the commercially identical items. The indicated quantity may be entered by the user as, for example, a number of the commercially identical items, or a proportion of the total quantity of the commercially identical items in the retail package. Alternatively, the indicated quantity may be such a quantity that was suggested to the user (e.g., by or via the mobile app) and accepted by the user via the mobile app.

Figure 1B:
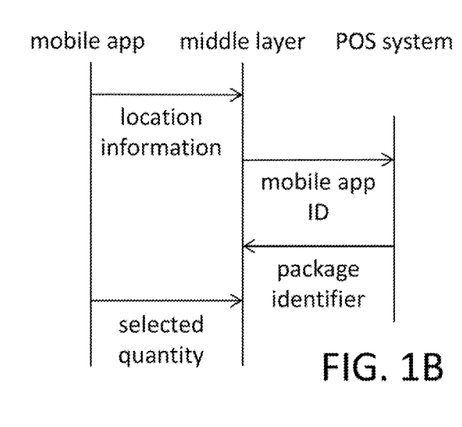
FIGS. 1B and 1C show diagrams of exchanges of data among a mobile app, a middle layer, and a POS system.
Figure 1C:
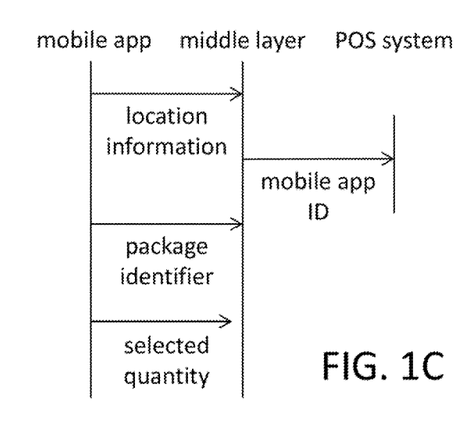

FIGS. 1B and 1C show diagrams of exchanges of data among a mobile app, a middle layer, and a POS system, in examples of uses of method MA100 as described above. First, the middle layer receives from the mobile app information indicating a current location of a mobile device on which the mobile app is resident. The middle layer then transmits, to a selected POS system, information that identifies the mobile app. The middle layer receives, from at least one among the POS system (FIG. 1B) and the mobile device (FIG. 1C), an indicator of a retail package that includes a plurality of commercially identical items. The middle layer also receives, from the mobile app, an indication of a quantity of the commercially identical items.

A middle layer ML100 may be used to perform method MA100. Such a middle layer may comprise software executing on one or more processors, using data stored in one or more storage elements (e.g., random-access memory, disk storage, etc.). For example, middle layer ML100 may include software components (e.g., services) executing on one or more servers and configured to receive data from one or more databases and/or to communicate with one or more data networks (e.g., via appropriate interfaces).

Figure 2:
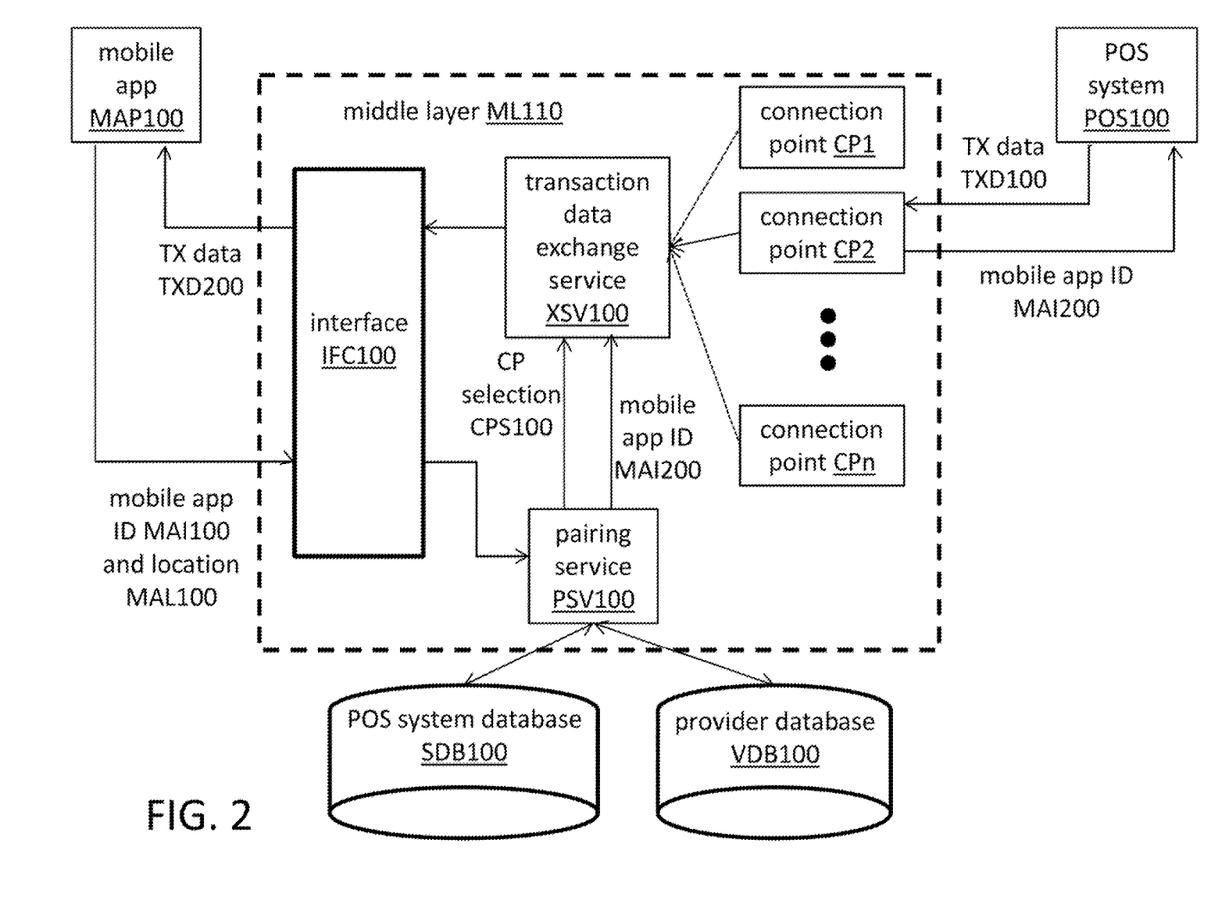
FIG. 2 includes a block diagram of an implementation ML110 of middle layer ML100.

FIG. 2 includes a block diagram of an implementation ML110 of middle layer ML100 that includes a pairing service PSV100 and a transaction data exchange service XSV100. From mobile app MAP100, pairing service PSV100 receives an identifier of the mobile app MAI100 and a location of the mobile app MAL100. Identifier MAI100 may be a label identifying a particular payment account (e.g., a credit card account number), a particular account of a particular retailer loyalty program, etc. Location MAL100 may be a label that indicates a current location (e.g., in GPS coordinates) of a mobile device upon which mobile app MAP100 is executing. Such data communication between mobile app MAP100 and middle layer ML100 may occur, for example, over one or more cellular data networks (e.g., 2G, 3G, 4G, LTE, etc.) and/or one or more local-and/or wide-area wireless data networks (e.g., IEEE 802.11 or WiFi). Such data communication between mobile app MAP100 and middle layer ML100 may occur, for example, via an interface IFC100 that may perform operations such as formatting, handshaking, etc.

Based on location MAL100, middle layer ML100 selects one among a plurality of POS systems. In one example, pairing service PSV100 is configured to use information from a database SDB100 that stores the locations of the POS systems (e.g., in GPS coordinates) to select a POS system that is within a threshold distance of location MAL100. It may be desirable to design the threshold distance to exclude transient situations, such as a user of the mobile device driving or walking past a POS system. For example, different threshold distances may be associated with different POS systems (e.g., a smaller threshold distance for a POS system in a store located along an urban street than for a POS system in a store along a rural highway). Additionally or alternatively, pairing service PSV100 may be implemented to select a POS system only after determining that a detection condition has persisted over a particular time period (e.g., two, four, five, eight, ten, fifteen, or sixteen seconds). Examples of such a threshold distance include two, four, five, eight, ten, twelve, sixteen, twenty, and thirty-two feet and one, two, four, five, eight, ten, twelve, and sixteen meters.

The plurality of POS systems may be limited to POS systems of a particular retailer or may include POS systems of a plurality of retailers. For example, pairing service PSV100 may be implemented to select a POS system of a retailer only if the mobile device is currently associated with an account of a loyalty program of the retailer. Such an association may be recorded, for example, in a corresponding entry of a provider database VDB100 that indicates whether the mobile device is associated with a particular retailer loyalty program (and if so, may indicate the account number as well).

POS systems may be configured to have closed architectures, such that an interface capable of exchanging data with a POS system of one type may be unable to exchange data with a POS system of another type. It may be desirable to configure middle layer ML100 to allow data exchange with more than one such type of POS system. As shown in FIG. 2, middle layer ML110 includes a plurality n of connection points CP1 to CPn, each of which may be implemented to support data exchange with a different respective type of POS system. In such case, preparation for use of middle layer ML110 with a new POS system may include configuring the POS system to connect to an appropriate one of the connection points and storing this association to POS system database SDB100. In one example, a POS system connects to the corresponding connection point through a uniform resource locator (URL) associated with the connection point.

Each of connection points CP1-CPn may be implemented to include, for example, a buffer into which data is expected to be written in a particular format. A connection point may also include software configured to verify that incoming data is properly formatted and possibly to return an error code to the data source in response to a determination that the incoming data does not conform to the respective format.

Figure 3A:
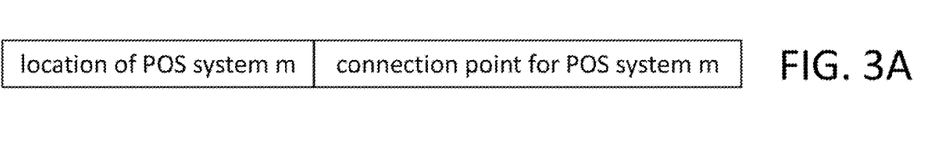
FIG. 3A shows an example of an entry in an implementation of POS system database SDB100.

Database SDB100 may be implemented to associate the location of a POS system with an appropriate one of the n connection points CP1-CPn. FIG. 3A shows an example of an entry in such an implementation of POS system database SDB100. This entry (e.g., the m-th in a total of M entries) associates the location of POS system m (e.g., in GPS coordinates) with a corresponding connection point (e.g., among connection points CP1-CPn) for POS system m. In some cases, the same connection point may be associated with all POS systems for a particular retailer, or with all POS systems within a particular region for a particular retailer.

Middle layer ML100 transmits, to the selected POS system, an identifier MAI200 of the mobile app. Identifier MAI200 may be the same as identifier MAI100. Alternatively, identifier MAI200 may identify the mobile app in a different context. In one such example, identifier MAI100 is a label identifying a particular payment account (e.g., a credit card account number) associated with mobile app MAP100. In this example, pairing service PSV100 is implemented to detect that the selected POS system is associated with a particular retailer, to use information from identifier MAI100 to retrieve an indication of a particular account of the retailer's loyalty program that is associated with the identified payment account (e.g., from a database), and to transmit a label identifying the associated loyalty program account to the selected POS system as identifier MAI200.

Middle layer ML110 may be implemented to select the connection point prior to transmission of identifier MAI200. In such case, identifier MAI200 may be forwarded to the selected POS system via the appropriate connection point. For example, pairing service PSV100 may be implemented to produce connection point selection CPS100 prior to transmission of identifier MAI200 (e.g., via the selected connection point).

When the mobile app associated with identifier MAI200 is used at the POS system for a purchase, the POS system recognizes the mobile app from identifier MAI200 (e.g., a label associated with the account being used for payment) and responds by forwarding transaction data of the purchase to the mobile app. Such forwarding may occur once the POS system has obtained approval for the purchase (e.g., from an issuer of a credit card account used for the purchase). It may be desirable for the pairing between the POS system and the mobile app to expire after a time period (e.g., after fifteen, sixteen, thirty, thirty-two, sixty, or sixty-four minutes) if the mobile app has not yet been presented at the POS system for payment. One or more of the POS system and the mobile app may also communicate with one or more services of a merchant service provider (e.g., of the retailer), such as a coupon service, a loyalty program service, and/or a payment service.

The transaction data includes information that identifies the retail package. Such information may include, for example, a product code such as a corresponding 12-digit UPC-A, UPC-B, or UPC-C code; a corresponding EAN-8 or EAN-13 code; or the like. Additionally or alternatively, such information may include a text description of the retail package. In one example, the transaction data includes a listing of the retail package and any other retail items purchased in the transaction and their respective prices (e.g., a receipt). The POS system may also be configured to include other information within the transaction data, such as an expiration date of the package.

The POS system may be configured to forward the transaction data to the mobile app by e-mail (e.g., in text format or as an attachment in text, HTML, or PDF format), by text messaging (e.g., Short Message Service or 'SMS'), or to a Uniform Resource Locator (URL) associated with the mobile app. In such cases, middle layer ML100 may receive information that identifies the retail package from the mobile app rather than from the POS system (or in addition to data TXD100).

Alternatively or additionally, the POS system may forward the transaction data to the mobile app via middle layer ML100. FIG. 2 shows one example of such forwarding in which transaction data exchange service XSV100 receives transaction data TXD100, via a connection point as indicated by connection point selection CPS100, and forwards the information (in a possibly different form TXD200) via interface IFC100 to the mobile app.

Transaction data exchange service XSV100 may be configured to filter data TXD100 to remove extraneous information. For example, if the transaction includes one or more items that are not to be offered for resale (e.g., a prescription medication, a single-serving beverage, etc.), transaction data exchange service XSV100 may remove information regarding such item or items from data TXD100 to produce data TXD200. It may be desired to exclude from resale items that require special handling (e.g., storage below room temperature) to remain effective. Such filtering by service XSV100 may include comparing a list of the purchased items to a list of items eligible for resale.

Instead of removing (e.g., by service XSV100) items that are not to be offered for resale, it may be desired to implement interface IFC100 to flag items that are eligible for resale (e.g., by comparing a list of the purchased items to a list of items eligible for resale). Additionally or alternatively, mobile app MAP100 may be implemented to perform such flagging. In either case, mobile app MAP100 may be implemented to display to the user a list of only the purchased items which are eligible for resale, or to display an indication of which items are eligible for resale among a displayed list of all of the retail items purchased in the transaction.

Figure 3B:
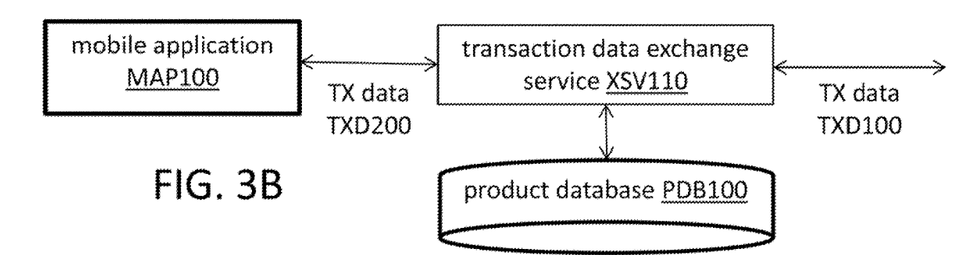
FIG. 3B shows an application of an implementation XSV110 of service XSV100.

Alternatively or additionally, one or more among transaction data exchange service XSV100 and interface IFC100 may be configured to include additional information associated with the retail package within data TXD200. The additional information may include such qualifiers and/or other details as, for example, brand name, manufacturer, expiration date, size, dose, barcode symbol, thumbnail image, product review, etc. FIG. 3B shows an application of an implementation XSV110 of service XSV100 that is configured to use data TXD100 (e.g., a UPC product code) to obtain such additional information associated with the retail package from a product database PDB100. Interface IFC100 may be similarly implemented. Additionally or alternatively, service XSV100 and/or interface IFC100 may be implemented to obtain such additional information through third-party application program interface (API) integration.

Service XSV100 or XSV110 and/or interface IFC100 may be implemented to include, within data TXD200, additional information associated with the mobile app. Such information may describe a current state of an inventory associated with the mobile app (e.g., a number of the same item that are currently offered for resale by the user), a history of sales from such inventory (e.g., a number of the same item that have been sold by the user during a recent time period, such as one, two, six, or twelve months), and/or other information that may be helpful to the user in deciding how much of the item to offer for resale.

Middle layer ML100 receives, from the mobile app and in response to the transaction data, an indication of a quantity of the commercially identical items. In one example, this indication is a number of the commercially identical items that a user of the mobile app wishes to offer for resale. In another example, this indication is a proportion of the total quantity of commercially identical items in the retail package (e.g., twenty-five, fifty, or seventy-five percent) that a user of the mobile app wishes to offer for resale. Such proportion may be based on the user's history. For example, if the user has historically chosen to offer fifty percent of the total quantity of pills in her purchases of Advil™ via the mobile app (or of ibuprofen, or of pain reliever medication), and the current purchase includes a bulk package of twenty Advil™ pills or packets, the mobile app may suggest offering ten of the individual items in the current purchase for resale.

Figure 3C:
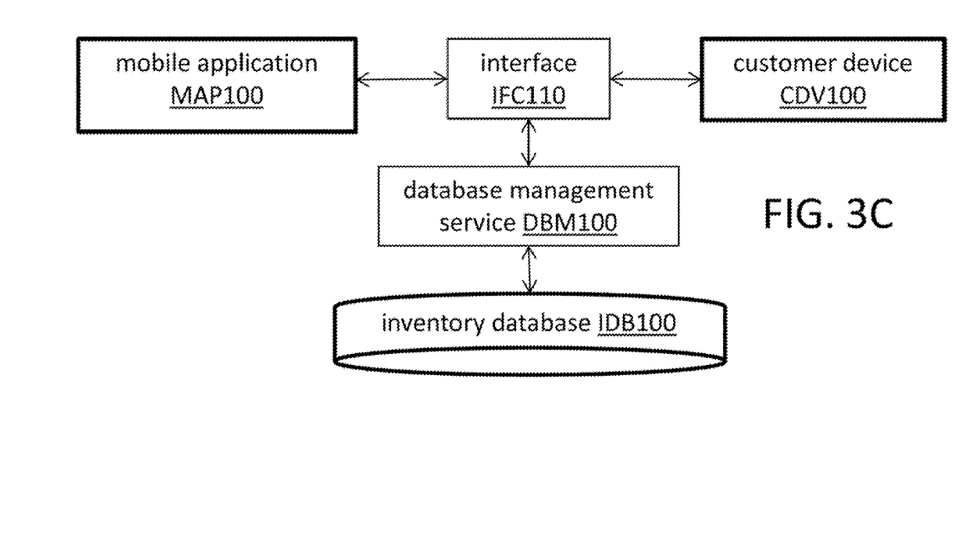
FIG. 3C shows an application of an implementation IFC110 of interface IFC100.

FIG. 3C shows an application of an implementation IFC110 of interface IFC100 that is configured to use the indicated quantity to update an inventory associated with the mobile app in an inventory database IDB100. Interface IFC110 may also be configured to respond to requests from a customer device CDV100 to purchase such an item. In this example, middle layer ML110 is also implemented to include a database management service DBM100 that updates database IDB100 in response to provider indications of items and quantity to be added and supports location- (e.g., map-) and/or category-based searches of database IDB100 in response to customer queries via interface IFC110.

An implementation of method MA100 or middle layer ML100 as described herein may be used to support post-retail resale of such commercially identical units in an automated manner, triggered by conditions such as the user's proximity to a vendor of products eligible for resale and by purchase of a listed item, that is transparent to the user provider. One example of a workflow is as follows:

1) A person using the mobile app goes to a retail store to purchase some general items, as well as over-the-counter medication and feminine hygiene items that he wants to add to his online inventory for resale of individual units. The user fills up his cart with these items and reaches the checkout counter. At the checkout counter, the POS system is connected to a cloud-based middle-ware system (e.g., an implementation of middle layer ML100) that also connects to the mobile app. Through the cloud-based system, the mobile app notifies the POS system of its location. The mobile app may also have an interface to connect to the store's loyalty system.

2) During checkout, the user taps on the mobile app to indicate that he wants to make the purchase through the mobile app and also to use the mobile app to list some portion of his current purchase as available for resale. The mobile app interfaces with the POS system and completes the transaction through an interface to a digital wallet that is also resident on the mobile device.

3) Post-purchase, the mobile app shows the list of items that the user has purchased and also a suggested flag to indicate which of these items he would probably add to his inventory for resale. The mobile app may also suggest quantities of those items to be offered for resale. For example, if the user historically preferred to sell fifty percent of his purchases of Advil™ through the online interface, and he currently purchased a retail package containing twenty individual packets of Advil, the mobile app may suggest uploading ten packets into the user's inventory.

Additionally or alternatively, the mobile app may suggest a unit price for the items. If the purchase includes more than one commercially distinct package of items that may be offered for resale (e.g., a package of Advil and a package of aspirin), the mobile app may suggest a corresponding unit price for the items in each such package. The mobile app may suggest a unit price for the items in a bulk package based on a unit cost of the items (e.g., the purchase price of the bulk package divided by the number of commercially identical items in the bulk package).

The mobile app may be configured to calculate the unit price by applying a markup factor to the unit cost (e.g., a factor of two or three), by adding a markup amount to the unit cost (e.g., fifty cents, one dollar, or two dollars), or by adding a markup amount after applying a markup factor. Alternatively, the mobile app may be configured to select a corresponding one among a set of unit prices based on the unit cost. In one such example, the mobile app selects a unit price of two dollars for items having a unit cost of up to twenty-five cents, a unit price of four dollars for items having a unit cost of up to one dollar, and a unit price of five dollars for items having a unit cost of up to two dollars.

Alternatively, the user may indicate a unit price for the items (or a corresponding unit price for the items in each commercially distinct package). For a case in which the mobile app suggests a unit price, the mobile app may be configured to default to the suggested unit price, or to use the suggested unit price only upon confirmation by the user, who may choose to enter a different unit price instead.

4) Once the user has verified the selection of items and quantity (and unit price, unless a default is assigned), the user's online provider inventory may be updated accordingly. Such inventory may be stored in a database of the cloud-based middle-ware system (e.g., an implementation of inventory database IDB100), and such update may be performed using a management service of the middle-ware system (e.g., an implementation of database management service DBM100), which may also be configured to automatically obtain details regarding the selected item such as the manufacturer and/or brand, item name, item quantity, barcode, expiry date, and/or product review, which may be obtained through third-party API integration.

Figure 4:
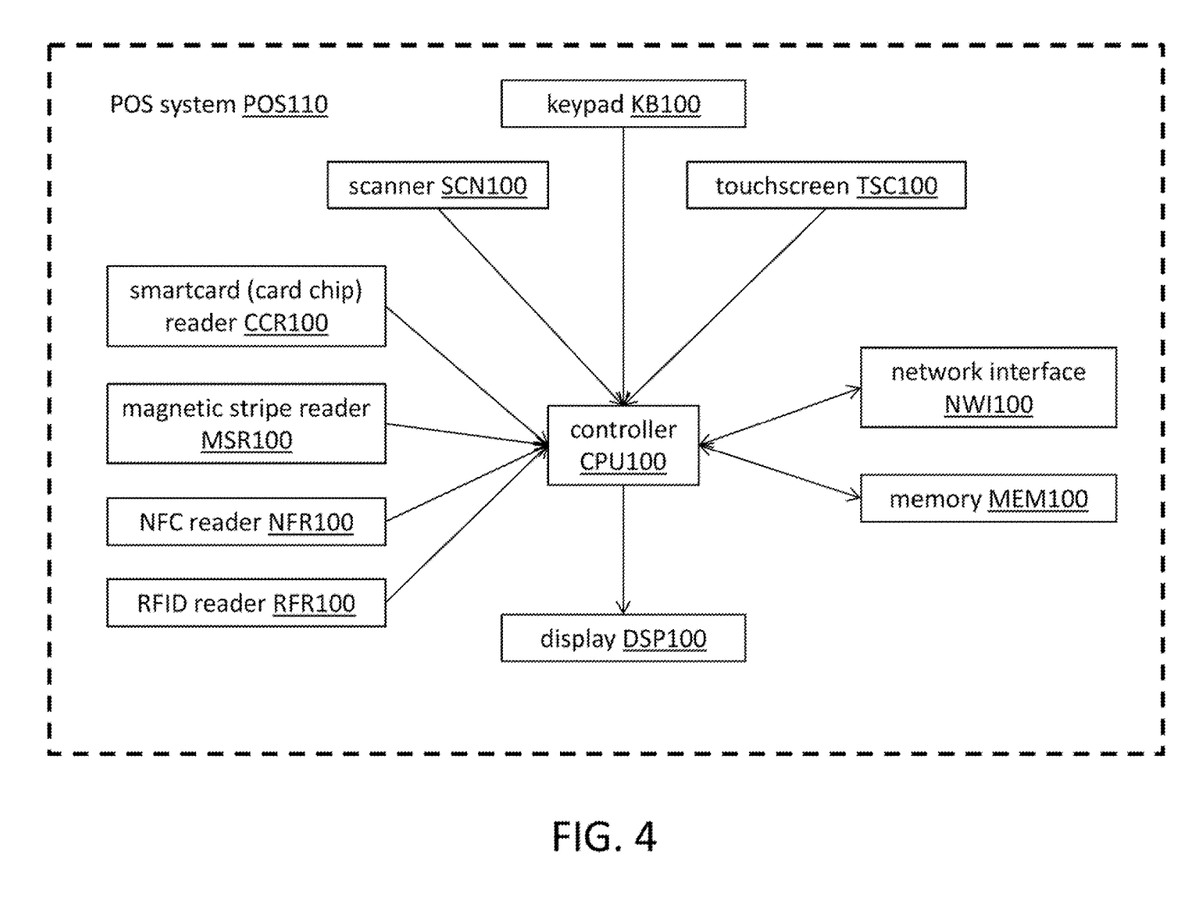
FIG. 4 shows a block diagram of an implementation POS110 of POS system POS100.

FIG. 4 shows a block diagram of an implementation POS110 of POS system POS100. In order to obtain payment information from a user of the mobile device (e.g., a payment card account number or other label, such as a token associated with such a number), POS system POS110 may include any one or more among the following: a magnetic stripe reader MSR100 configured to read a magnetic stripe of a payment card (e.g., a credit card, a debit card, a stored value card); a smartcard or card chip reader CCR100 configured to communicate (by direct physical contact or contactlessly) with a circuit embedded in a payment card; a near-field-communications (NFC) reader NFR100 configured to communicate contactlessly with an NFC tag and/or a mobile device (e.g., according to a standard such as ISO/IEC 18092, ECMA-340, and/or Bluetooth); and an RFID reader RFR100 configured to communicate contactlessly with an RFID tag and/or a mobile device (e.g., according to a standard such as ISO/IEC 14443 and/or ISO/IEC 18000-3). For example, POS system POS110 may be configured to support any one or more of the following contactless payment methods: MasterCard PayPass™, American Express ExpressPay™, Visa payWave™, Google Wallet™, and Apple Pay™. POS system POS110 may also include a cash drawer for handling cash transactions.

POS system POS110 may also include one or more input devices, such as a scanner SCN100 configured to read product barcodes and a keypad KB100 and/or touchscreen TSC100 configured to receive user input. POS system POS110 may also include one or more output devices, such as a display DSP100 and/or a receipt printer (not shown).

POS system POS110 also includes at least one controller CPU100 (e.g., one or more microprocessors) and memory MEM100. Typical additional components not shown in FIG. 4 include an operating system, and hardware and software interfaces configured to allow controller CPU100 and the operating system to communicate with the various other components. POS system POS110 also includes a network interface NWI100 configured to receive mobile app ID MAI200 and to transmit transaction data TXD100 via one or more data networks, such as one or more cellular data networks (e.g., 2G, 3G, 4G, LTE, etc.) and/or one or more local- and/or wide-area wireless data networks (e.g., Bluetooth, IEEE 802.11 or WiFi).

System POS110 may be implemented to include a tablet computer. Such a tablet will typically contain at least controller CPU100, memory MEM100, touchscreen TSC100, display DSP100, and network interface NWI100, with each of one or more of the other components of system POS110 as described above being integrated into the tablet or attached to such a tablet (e.g., as peripherals) via a cable (e.g., a USB cable) or wirelessly (e.g., via Bluetooth).

Figure 5A:
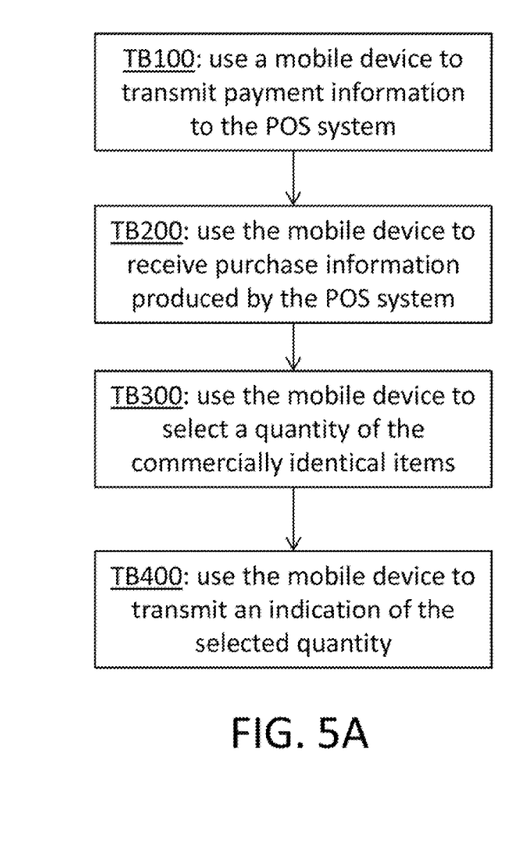
FIG. 5A shows a flowchart for a method MB100 of using a mobile device to purchase a retail package and to update an inventory to include items within the retail package.

FIG. 5A shows a flowchart for a method MB100 of using a mobile device to purchase a retail package and to update an inventory to include items within the retail package. Such method may be performed, for example, by a mobile app executing on a mobile device (e.g., an implementation of mobile app MAP100 as described above). The mobile app may be configured to execute within a mobile operating system resident on the phone, such as a version of Android (Google), iOS (Apple Corp.), or Windows Phone (Microsoft). It may be desirable for the mobile app to have access to a location of the mobile device (e.g., as GPS coordinates). It may be desirable for the mobile app to have the ability to initiate instances of a secure payment application resident on the mobile device (e.g., a digital wallet, such as MasterPass™ (MasterCard), Google Wallet™, or ApplePay™).

Method MB100 includes tasks TB100, TB200, TB300, and TB400. Task TB100 uses the mobile device to transmit payment information for a transaction to a POS system. Task TB100 may be performed at a retail location. The mobile app may perform task TB100 by causing a secure payment application to execute on the mobile device. For example, task TB100 may use the mobile device to transmit the payment information over a near-field-communication (NFC) channel. The payment information may include a credit card account number or a token associated with such an account number.

Task TB200 uses the mobile device to receive purchase information for the transaction that identifies a retail package, purchased in the transaction, that includes a plurality of commercially identical items as described herein. Such information is produced by the POS system upon approval of payment, and may be received by the mobile device from the POS system or via an intermediate entity, such as a middle layer ML100 as described herein. Task TB200 may include receiving the purchase information over an NFC channel (e.g., the same or different than an NFC channel used to carry the payment information), one or more cellular data networks (e.g., 2G, 3G, 4G, LTE, etc.) and/or one or more local- and/or wide-area wireless data networks (e.g., IEEE 802.11 or WiFi). Task TB200 may include receiving the purchase information as a text e-mail, as an attachment in text, HTML, or PDF format to an e-mail, by text messaging (e.g., SMS), or to a URL associated with the mobile app. In one example, the purchase information is the UPC product code of the retail package. In another example, the purchase information is received in the form of a receipt of the transaction that identifies the retail package (e.g., UPC product code and a brief description) and may also include the price paid for the package.

Method MB200 may also include using the mobile device to receive (e.g., from the POS system and/or from a middle layer as described herein) other information such as any of the following: a total quantity in the package, a thumbnail or other image of the package and/or of the individual items within it, a description of the product, expiration date, etc. Such information may be retrieved, for example, by a service of the middle layer from an implementation of product database PDB100 as described above and/or from a similar product database of the retailer (e.g., via lookup using the UPC product code and/or stock-keeping unit (SKU) number). Alternatively or additionally, method MB200 may include using the mobile device and the UPC product code of the retail package to obtain such other information (e.g., via online search and/or a third-party online database).

Figure 5B:
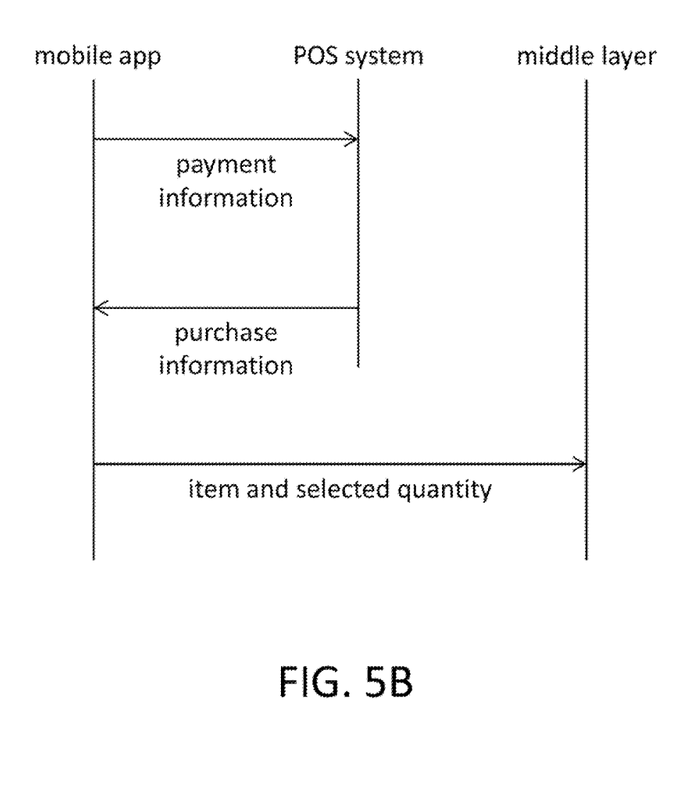
FIG. 5B shows a diagram of exchanges of data among a mobile app, a POS system, and a middle layer.

Task TB300 uses the mobile device to select a quantity of the commercially identical items of the retail package. As described above, the mobile app may be configured to suggest a quantity (e.g., based on a history of the user's activity) and/or to allow selection of the quantity as a proportion of the total quantity of individual items in the retail package. Task TB300 may also include using the mobile device to select a unit price for the items. As described above, the mobile app may be configured to suggest such a price, which may be selected by default. Task TB400 uses the mobile device to transmit a command to update an inventory associated with the user to include the selected quantity of the commercially identical items. FIG. 5B shows a diagram of exchanges of data among a mobile app, a POS system, and a middle layer in an example of a use of method MB100 as described above.

Figure 6:
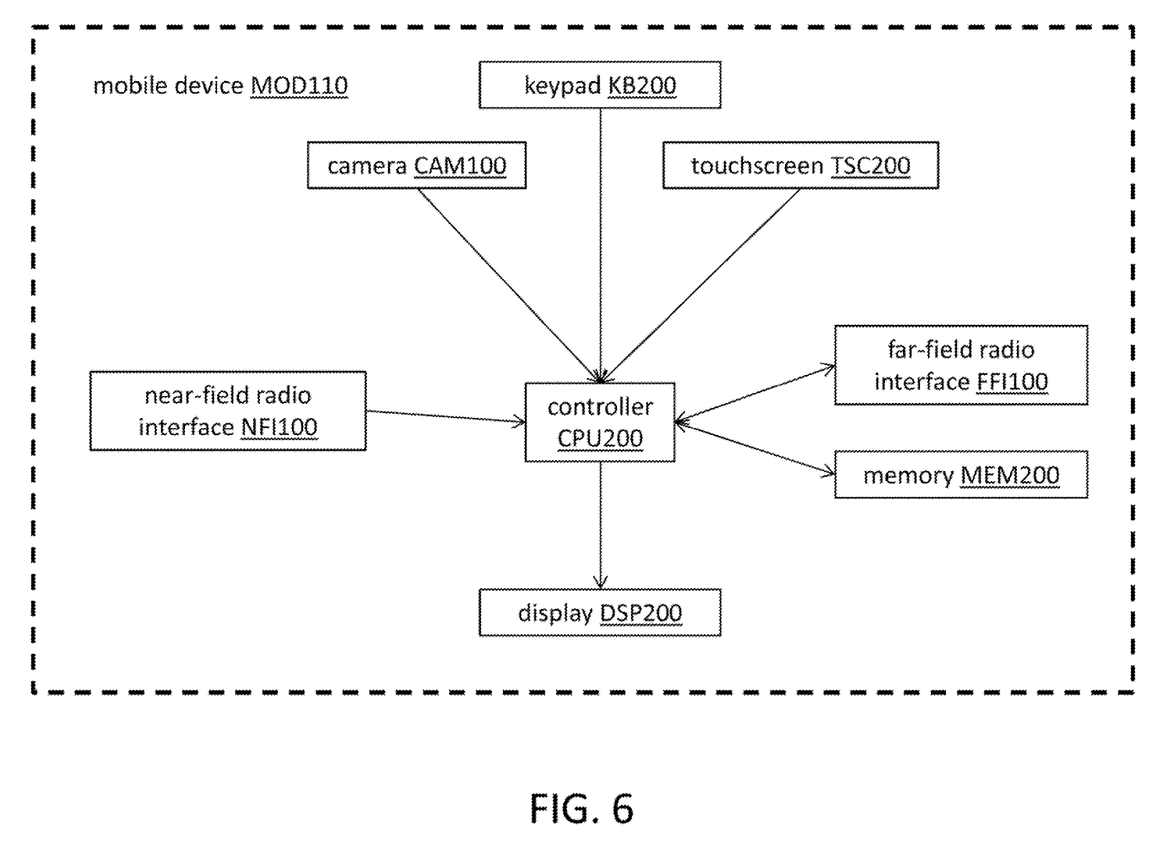
FIG. 6 shows a block diagram of an implementation MOD110 of mobile device MOD100.

FIG. 6 shows a block diagram of an implementation MOD110 of mobile device MOD100 on which a mobile app as described herein may be resident. In order to provide payment information to a POS system, mobile device MOD110 may include one or more payment interfaces, such as a near-field radio interface NFI100 configured to communicate contactlessly with the POS system (e.g., according to an NFC standard, such as ISO/IEC 18092, ECMA-340, and/or Bluetooth, and/or an RFID standard, such as ISO/IEC 14443 and/or ISO/IEC 18000-3).

Device MOD110 includes a display DSP200 configured to provide output to the user (e.g., as produced by the mobile app). Display DSP200 may also be implemented to display a QR code for presentation to the POS system as payment information. Device MOD110 includes one or more input devices, such as touchscreen TSC200 and/or keypad KB200, that may be used for interacting with the mobile app, for entering a selected quantity or proportion for resale, and/or for confirming a quantity or proportion suggested by the mobile app. Device MOD110 may include a camera CAM100 that the user may use to take a photo of the retail package (and/or of one or more of the individual items) to be added to the listing for resale.

A wireless network to which device MOD110 is connected may be configured to determine the location of the device (e.g., by cellular triangulation, WiFi triangulation, HPS, assisted GPS, and/or any combination of one or more such methods) and provide it to the device. Device MOD110 may then transmit this location (or a location based thereon) as location MAL100. Additionally or alternatively, for purposes of obtaining location MAL100, mobile device MOD110 may include a GPS receiver and antenna (not shown).

Device MOD110 also includes at least one controller CPU200 (e.g., at least one microprocessor) configured to execute the mobile app MAP100 and a memory MEM200 configured to store instructions and data of the mobile app. Device MOD110 may also include a digital wallet app configured to execute on controller CPU200 and to provide payment information (e.g., a number of a payment card account linked to the digital wallet, or another label, such as a token associated with such an account). Such a digital wallet app may be configured to perform a card emulation operation (e.g., host card emulation or HCE). Memory MEM200 may also include secure storage (e.g., a secure element) to support such a digital wallet app. Device MOD110 may include a fingerprint reader and/or other user authentication device configured to provide authentication data to such a digital wallet app.

Mobile device MOD110 also includes a far-field radio interface FFI100 configured to transmit mobile app ID MAI100 and location MAL100 and to receive transaction data TXD200 via one or more data networks, such as one or more cellular data networks (e.g., 2G, 3G, 4G, LTE, etc.) and/or one or more local- and/or wide-area wireless data networks (e.g., Bluetooth, IEEE 802.11 or WiFi). Typical additional components of mobile device MOD110 that are not shown in FIG. 6 include a mobile operating system, such as a version of Android (Google), iOS (Apple Corp.), or Windows Phone (Microsoft), and hardware and software interfaces configured to allow controller CPU200 and the operating system to communicate with the various other components.

As described above, method MB100 may be performed by a mobile app executing on a smartphone and communicating over a broadband cellular data network. Similarly, purchases from such an inventory may also be performed using a mobile app, or via a web-based interface, on a customer device CDV100 (e.g., a smartphone) communicating over a broadband cellular data network. For example, mobile app MAP100 may be implemented to support both uploading of a provider account and purchase from the online inventory, with the particular user choosing to use the app at one time to list items as a provider, and at another time to browse and/or purchase such items from others.

Middle layer ML100 may be implemented to support, on the customer side, a map-based search to identify one or more providers based on the customer's current location and the item requested. Provider database VDB100 may be implemented to include ratings for each provider, which may include an overall rating for the provider and/or a provider rating relating to particular categories of goods, and interface IFC100 may be implemented to provide appropriate ratings to the customer prior to purchase. Mobile app MAP100 may be implemented to allow the customer to pay for such a purchase with a payment card that is on file, such as in a digital wallet app resident on the mobile device (e.g., MasterPass). Once the purchase has been completed, the mobile app may also allow the customer to enter one or more ratings for the provider.

In one scenario, a student ("John") staying at a college dormitory is in desperate need of a pain reliever (e.g., an aspirin or Advil™). The local store is few miles away, but there are twenty other students living in the dormitory, and there is a chance that one of them would have a spare Advil™ or similar item. It is possible that John already has a box of Advil™ that has expired because he doesn't use the product very often, and purchase of a single dosage is not available.

In this situation, interface IFC100 may be implemented to provide a location-based search, based on John's current location, to allow John to search for a single (unexpired) dosage of Advil™ and to find someone nearby who has that item. Additionally he can pay directly through a payment card on file (e.g., in a digital wallet associated with the mobile device, such as MasterPass). In such manner, the system could save John a trip to the store and also allow him to purchase medication for single usage rather than buying it in bulk.

Mobile app MAP100 may be implemented to support such a process by displaying a menu of items from which the customer may indicate her request. For example, the mobile app may allow the customer to select a specific item (e.g., ibuprofen) or a category of items (e.g., pain reliever). Once the selection has been made, the mobile app sends the customer's request and location to interface IFC100.

In response to the request, middle layer ML100 may reference provider database VDB100 and inventory database IDB100 to identify at least one nearby provider (if any) that currently has the requested item, or any items within the requested category, within its inventory. Via interface IFC100, middle layer ML100 may send the names and corresponding locations of the identified providers to the mobile app. The search results sent to the mobile app by middle layer ML100 may also include other information for each corresponding provider, such as ratings, item prices, and/or quantity available of the requested items.

The mobile app then displays the results to the customer (e.g., sorted by distance, with the closest matching provider displayed first). For a case in which the request indicated a category, the mobile app may prepare the search results for display by breaking down results for the category (e.g., feminine hygiene) into results for the commercially distinct items within the category (e.g., tampons, sanitary napkins).

The customer then places an order by selecting, from among the displayed results, a particular item from a particular provider. Once the selection has been made, the mobile app sends the customer's order to interface IFC100. In response to the order, the middle layer sends a notification of the order to the provider and a confirmation of the order to the customer. Such notification and confirmation may be sent, for example, via the mobile app, text messaging, automated voice telephone call, and/or e-mail. The mobile app and middle layer may also be configured to allow the customer and provider to communicate directly via the middle layer (e.g., by text, audio, and/or video) if necessary to complete the purchase. As noted above, payment by the customer may be accomplished via a payment card on file. The middle layer may also be implemented to send a follow-up request to the customer (e.g., via the mobile app, SMS, and/or e-mail) to enter a rating for the provider.

It may be desirable to extend a system and method for resale of personal care items in order to provide access to these important items in locations (e.g., of developing countries) that are not penetrated by medical retailers. Due to lack of facilities and infrastructure, for example, providing medical solutions to rural areas in developing countries has always been difficult. As noted above, extending support for such resale may also help to reduce the problem of medication expiration resulting from a retail availability that is limited to bulk packaging rather than single-dose packaging.

It may be desirable to support such resale even in the absence of a network infrastructure as described above, such as in an area where only voice calling and text messaging is available. For example, it may be desirable to provide a similar service via text-based interaction by a customer device (e.g., by SMS or other text messaging service), such that a feature phone is sufficient even if a smartphone is not available. Although smartphones may be scarce in developing countries, such regions typically have a deep penetration of feature phones. For example, in 2014 the penetration of mobile phones in India and sub-Saharan Africa was 77.58% and approximately 70%, respectively.

A cloud-based system providing such service may be implemented to allow an individual to add his or her inventory to the system using text messaging. The system may also be implemented to support use of a web-based platform if available. The products to be added by the user may have been purchased at retail (e.g., via a POS system as described above), or online or otherwise.

Figure 7A:
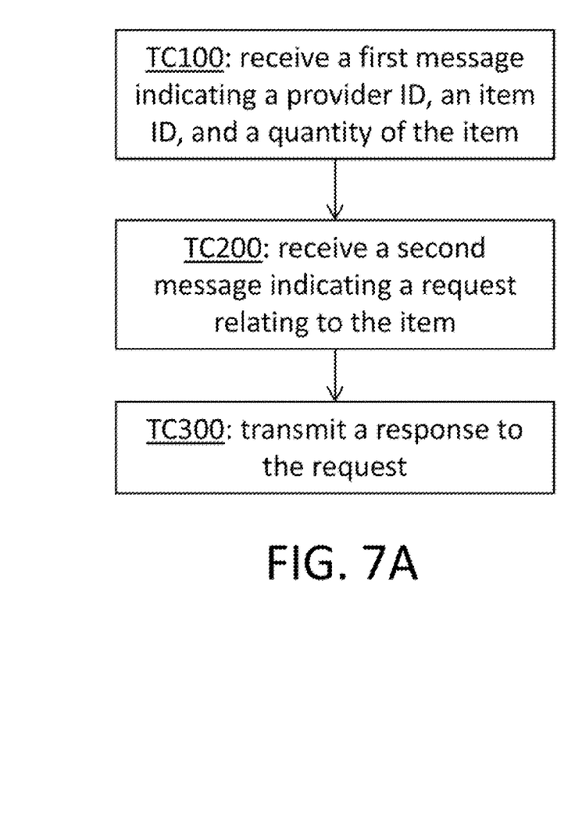
FIG. 7A shows a flowchart of a method MC100 of maintaining an inventory of items and corresponding providers and of responding to customer requests relating to the items.

The cloud-based system (e.g., an implementation of middle layer ML100) may also include a layer that organizes the personal care items by category and/or by the symptoms that it may be used to address. In such one example, a customer texts that he or she has one or more particular symptoms (e.g., a fever with dry throat). The system may be configured to suggest medication for that ailment by identifying one or more products that address such symptoms (e.g., according to a predetermined association stored in an implementation of product database PDB100). Based on the customer's location, the system may identify one or more providers that are local to the customer (e.g., as indicated by an implementation of provider database VDB100). Such provider identification may include performing a map-based search. The customer's location may have been previously entered into the system by the customer, may be obtained from a subscriber account associated with the customer's subscriber number, or may be provided by the customer in the first text message or in response to a text message request from the cloud-based system. It may be desired to implement method MC100 to permit a customer to indicate (e.g., within the request message or in a separate message) a selection among multiple locations on file (e.g., between a home location and an office location).

If a unit of the identified product is found within the inventory of a local provider (e.g., as indicated by an implementation of inventory database IDB100), the system may send a text message to the customer that includes the contact number of at least one such provider. The message may also include the name of the identified item, its cost, and/or one or more ratings of each provider (e.g., an overall rating, a category-specific rating). Such an operation of providing a symptom-based recommendation may be limited according to the geography and/or jurisdiction of the customer's location (e.g., in order to comply with local regulations relating to practice of medicine).

The system may be configured to support cashless transactions. In one example, the cloud-based system is configured to allow the customer to pay for the item using a mobile-phone-based money transfer service, such as M-Pesa. Alternatively or additionally, the cloud-based system may be configured to allow the customer to pay for the item by drawing from a prepaid account (e.g., using a personal identification number (PIN) that is linked to the mobile device).

FIG. 7A shows a flowchart of a method MC100 of maintaining an inventory of items (e.g., personal care items) and corresponding providers and of responding to customer requests relating to the items. Such a method may be performed, for example, by a cloud-based system (e.g., an implementation of a middle layer as described herein).

Method MC100 includes tasks TC100, TC200, and TC300. Task TC100 receives a first text message, from a first subscriber number. A subscriber number may be, for example, a telephone number that has been assigned by a cellular telecommunications provider to a particular mobile device (e.g., to a Subscriber Identity Module (SIM) within the device). The first text message identifies a provider, an item, and a quantity of commercially identical units within the item. The provider may be identified by the first subscriber number. Additional identification may be included in the first text message and/or in a follow-up message, such as an account number and/or a personal identification number (PIN) assigned to the provider by the cloud-based service (e.g., an implementation of middle layer ML100 as described herein). The item may be identified, for example, by a product code of the item (e.g., a UPC product code of a retail package). In such case, the product code may be obtained by the user by scanning or otherwise imaging the package (e.g., using a camera of a smartphone or feature phone). Where such service is available, such an image of the code may be sent by the user as an attachment to the text message, for extraction of the code by the cloud-based service. The quantity may indicate a number of the commercially identical items within the retail package and/or a proportion of the total number of such items within the package. The first text message may also include a unit price for the item. Alternatively, a unit price for the item may already be stored within the system and/or the provider may indicate the unit price in a different text message that identifies the item.

Figure 7B:
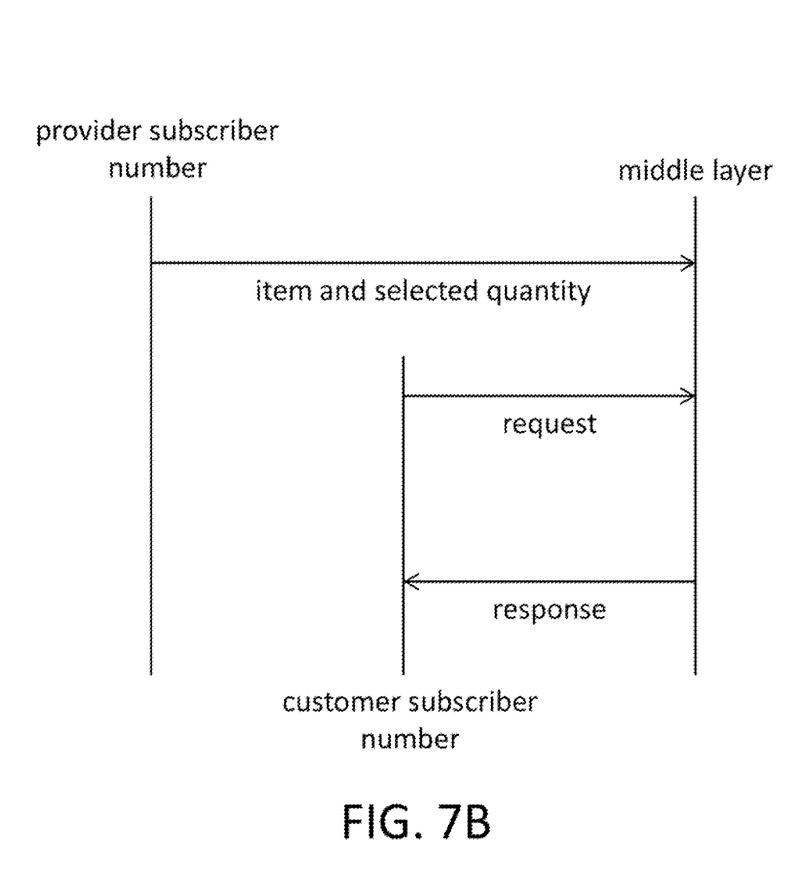
FIG. 7B shows a diagram of exchanges of data among a provider subscriber number, a middle layer, and a customer subscriber number.

Task TC200 receives a second text message, from a second subscriber number, that indicates a request relating to the item. In one example, the request is a description of at least one symptom that is associated (e.g., within the cloud-based system) with the item. Task TC300 transmits, to the second subscriber number, a response to the request. For example, the response may indicate an availability of at least one of the commercially identical items and/or may identify the provider (e.g., may include the first subscriber number). The response may also include a unit price for the item. FIG. 7B shows a diagram of exchanges of data among a provider subscriber number, a middle layer, and a customer subscriber number in an example of a use of method MC100 as described above. Method MC100 may also be implemented to include a subsequent task TC400, which receives a third text message from the second subscriber number, indicating the customer's order for the item, and in response transmits a fourth text message to the first subscriber number which notifies the provider of the customer's order.

An apparatus as disclosed herein (e.g., mobile device MOD100, POS system POS100, any among the elements of middle layer ML110) may be implemented in any combination of hardware with software, and/or with firmware, that is deemed suitable for the intended application. It is noted that the various methods disclosed herein (e.g., any among methods MA100, MB100, and MC100) may be performed by one or more processors. The implementations of methods, schemes, and techniques disclosed herein (e.g., any among methods MA100, MB100, and MC100) may also be embodied, in one or more computer-readable storage media, as one or more sets of instructions readable and/or executable by one or more processors, such that the instructions cause one or more processors executing the instructions to perform the acts of such a method as disclosed herein. Such a storage medium may be a conventional read/write memory such as a magnetic disk, floppy disk, optical disc, compact-disc read-only-memory (CD-ROM), digital versatile disc (DVD), Blu-ray Disc™, magneto-optical storage, flash memory, random-access memory, transistor-based memory, magnetic tape, and/or any other non-transitory computer-readable memory device as is known in the art for storing and retrieving data. Significantly, such computer-readable storage media may be remotely located from such one or more processors and may be connected to such one or more processors via a network such as a local area network (LAN), a wide area network (WAN), or the Internet.

It is understood by those skilled in the art that instructions for such method embodiments may be stored on their respective computer-readable memory and executed by their respective processors. It is understood by those skilled in the art that other equivalent implementations can exist without departing from the spirit or claims of the invention.

The previous description of the embodiments is provided to enable any person skilled in the art to practice the disclosure. The various modifications to these embodiments will be readily apparent to those skilled in the art, and the generic principles defined herein may be applied to other embodiments without the use of inventive faculty. Thus, the present disclosure is not intended to be limited to the embodiments shown herein, but is to be accorded the widest scope consistent with the principles and novel features disclosed herein.

What is claimed is:

1. A method comprising:
receiving, at a middle layer computing device via a first mobile device, location data indicative of a location of the first mobile device and an instance identifier associated with a mobile application executing on the first mobile device;
determining, at the middle layer computing device, based on the location of the first mobile device and a database comprising location information for a plurality of retail establishments, a first retail establishment of the plurality of retail establishments, wherein the first retail establishment is located at most a threshold distance away from the location of the first mobile device;
transmitting, by the middle layer computing device to a point-of-sale (POS) system of the first retail establishment, the instance identifier;
receiving, at the middle layer computing device via the first mobile device, an indication of a packaged product and a quantity of units of the packaged product, wherein the packaged product is purchased by a user of the first mobile device from the first retail establishment;
updating, at the middle layer computing device, based on the instance identifier and the quantity of units associated with the packaged product, an inventory database record to reflect with quantity of units of the packaged product, wherein the inventory database record is associated with the user of the first mobile device;
receiving, at the middle layer computing device via a mobile wallet associated with a second mobile device, an indication of a purchase of at least a portion of the quantity of units of the packaged product, wherein the portion of the quantity of units of the packaged product is purchased by a user of the second mobile device from the user of the first mobile device; and
updating, at the middle layer computing device, based the indication of the purchase of the portion of the quantity of units of the packaged product, the inventory database record to reflect a remaining quantity of units of the packaged product.

2. The method of claim 1, wherein the instance identifier comprises a label number that identifies at least one of an account of a loyalty program of the first retail establishment or a payment account number.

3. The method of claim 1, further comprising transmitting, by the middle layer computing device to the first mobile device, an indication of a suggested quantity of units of the packaged product.

4. The method of claim 1, further comprising selecting one of a plurality of locations of the first retail establishment.

5. The method of claim 4, wherein the instance identifier is transmitted to the POS system of the selected location of the first retail.

6. The method of claim 1, wherein receiving the indication of the packaged product and the quantity of units of the packaged product indicates completion of a purchase transaction between the POS system of the first retail establishment and the user of the first mobile device.

7. The method of claim 1, further comprising:
receiving, at the middle layer computing device via the second mobile device, a request to purchase a desired quantity of units of the packaged product;
determining, at the middle layer computing device, based on a query of the inventory database record, that the desired quantity of units of the packaged product is less than or equal to the quantity of units of the packaged product reflected by the updated inventor database record;
providing, by the middle layer computing device, based on a location of the second mobile device and a current location of the first mobile device, an indication that the user of the first mobile device has the desired quantity of units of the packaged product available for purchase.

8. The method of claim 4, wherein selecting one of a plurality of locations of the first retail establishment further comprises:
determining, for each of the plurality of locations of the first retail establishment, a respective distance from the location of the first mobile device.

9. The method of claim 8, further comprising:
determining, based on the threshold distance and each respective distance from the location of the first mobile device, a first location of the plurality of locations of the first retail establishment having a least respective distance from the location of the first mobile device.

10. The method of claim 1, wherein the middle layer computing device facilitates communication between the first mobile device and the POS system of the first retail establishment.

* * * * *